June 17, 1969 F. W. ANDERSON Plant Pat. 2,896
NECTARINE TREE
Filed Dec. 6, 1967
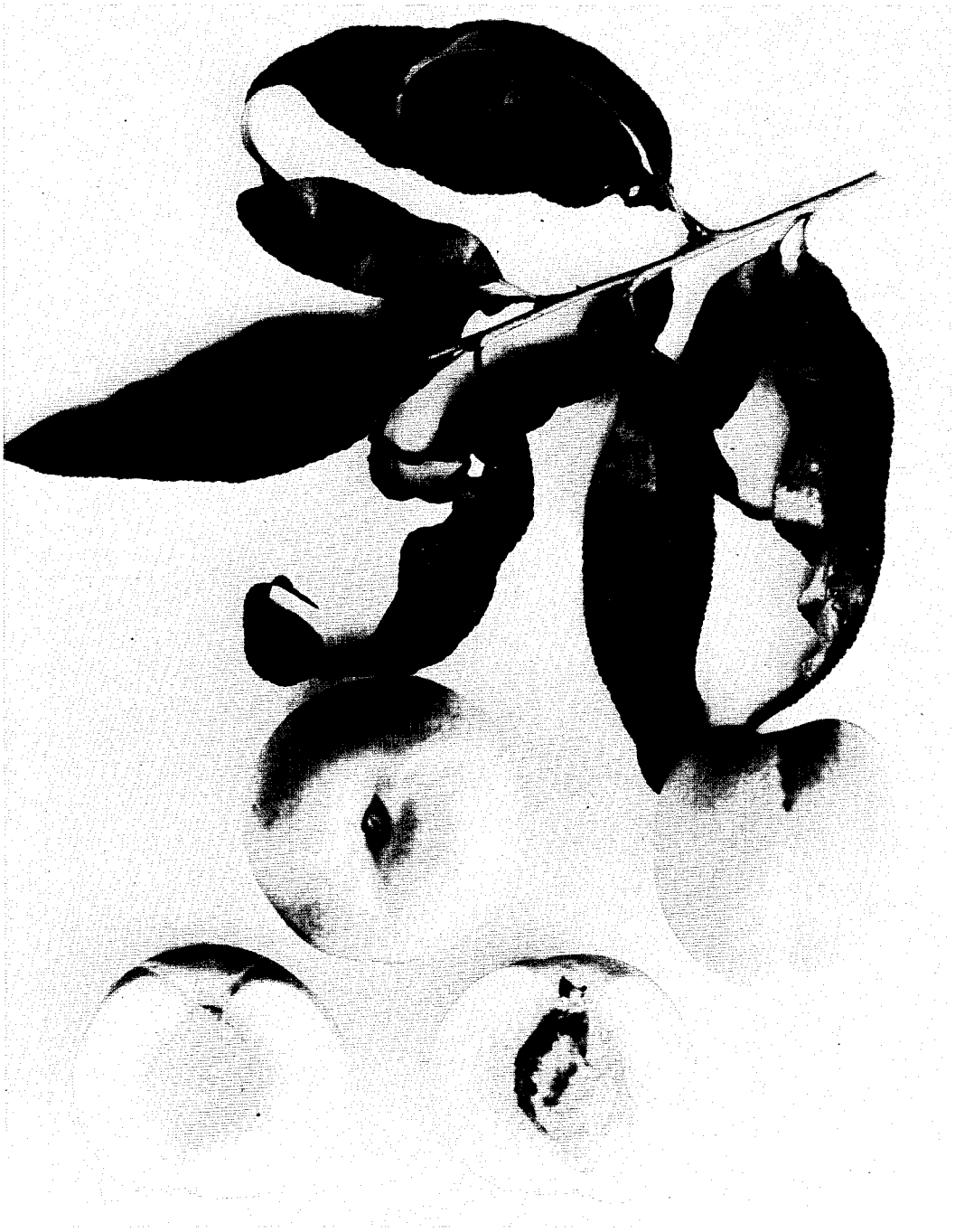
INVENTOR
Frederic W. Anderson
BY Webster & Webster
ATTORNEYS United States Patent Office Plant Pat. 2,896
Patented June 17, 1969

2,896
NECTARINE TREE

Frederic W. Anderson, Merced, Calif., assignor to Reedley Nursery, Inc., Reedley, Calif., a corporation of California Filed Dec. 6, 1967, Ser. No. 695,293
Int. Cl. A01h 5/08
U.S. Cl. Plt.—41 1 Claim

ABSTRACT OF THE DISCLOSURE

A nectarine tree, of medium size and vigorous growth, which is a regular and productive bearer of late ripening clingstone fruit having yellow flesh, and yellow skin substantially overspread with red at maturity; the fruit being large in size and globose in form.

*Classification of the variety*

The present variety of nectarine tree is embraced by Group 123 of the classification established by Caillavet and Souty in their Monographie des Principales Variétés de Pêchers, 1950 edition.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present variety of nectarine tree was originated by me in my experimental nursery and orchard located as aforesaid, as a first generation cross between the Late Le Grand nectarine (United States Plant Patent No. 1,035) and an unnamed seedling of the Gold King nectarine (United States Plant Patent No. 1,424). When—under close and continuing observation—one seedling of such cross evidenced certain desirable characteristics and which seedling is the present variety. I selected it for asexual reproduction, preparatory to commercialization.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

The present variety of nectarine tree, which is of medium size and vigorous growth, is a regular and productive bearer of large, globose, late ripening clingstone fruit having yellow flesh, and yellow skin substantially overspread with red at maturity; the instant variety being generally similar to the September Grand nectarine (United States Plant Patent No. 1,755) and ripens at approximately the same time, but in comparison the fruit is more attractive in appearance and much less susceptible to growth cracks and decay.

*Brief description of the drawing*

The drawing is an illustration, by photographic reproduction in color, of a twig with leaves, and detached fruit; one fruit being cut in half to expose the flesh, and with the stone remaining in one cut half.

*Description of the variety*

The botanical details of this new and distinct variety of nectarine tree—with color definitions (except those in common color terms) referenced to Maerz and Paul Dictionary of Color—are as follows:

Tree:
- *Size.*—Medium.
- *Vigor.*—Vigorous.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Red to green.

Leaves:
- *Size.*—Large to medium. Average length—5". Average width—1⅜".
- *Form.*—Lanceolate; abruptly pointed.
- *Thickness.*—Medium.
- *Margin.*—Crenate.
- *Petiole.*—Medium length—average ½". Medium thickness.
- *Glands.*—Average number and position—usually 1 to 3 on petiole, and 2 to 4 on blade. Medium size; reniform.
- *Color.*—Top side—medium green (23–L–7). Under side—lighter green (22–L–5).

Flower Buds: Size.—medium.

Flowers:
- *Blooming period.*—Date of first bloom—Mar. 7, 1967. Date of full bloom—Mar. 15, 1967.
- *Size.*—Large; showy.
- *Color.*—Pink.

Fruit:
- *Maturity when described.*—Eating ripe—Sept. 24, 1967.
- *Date of first picking.*—Sept. 14, 1967.
- *Date of last picking.*—Sept. 26, 1967.
- *Size.*—Uniform; large. Average diameter axially—3". Average transversely in suture plane—2⅞".
- *Form.*—Uniform; symmetrical; globose.
- *Suture.*—A conspicuous line extending from base to apex.
- *Ventral surface.*—Rounded.
- *Cavity.*—Rounded.
- *Base.*—Rounded.
- *Apex.*—Depressed.
- *Pistil point.*—Absent.

Skin:
- *Thickness.*—Thick to medium.
- *Tendency to crack.*—Slight; substantially less than September Grand.
- *Down.*—Wanting.
- *Color.*—Yellow (10–L–5) substantially overspread with red (5–L–5) at maturity, streaked and mottled darker red (7–L–6).

Flesh:
- *Juice.*—Moderate.
- *Texture.*—Firm; meaty.
- *Ripens.*—Evenly.
- *Flavor.*—Subacid.
- *Eating quality.*—Good.
- *Color.*—Yellow (10–L–4). Surface of pit cavity—red (5–L–5) lightly streaked into flesh.

Stone:
- *Type.*—Cling; adheres to flesh over entire surface.
- *Size.*—Large. Average length—1⅜". Average breadth—1⅛". Average thickness—⅞".
- *Form.*—Oblong to oval.
- *Sides.*—Equal.
- *Tendency to split.*—Slight.

*Color.*—Garnet red (7–J–6).
Use: Market; dessert; long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of nectarine tree, substantially as illustrated and described, which is of medium size, vigorous growth, and a regular and productive bearer of large, globose, late ripening clingstone fruit having yellow flesh, and yellow skin substantially overspread with red at maturity; the variety being characterized by general resemblance to the September Grand nectarine and bearing fruit ripening at approximately the same time but in comparison such fruit is more attractive in appearance and much less susceptible to growth cracks and decay.

No references cited.

ROBERT E. BAGWILL, *Primary Examiner.*